(12) United States Patent
McDonald

(10) Patent No.: US 9,173,720 B2
(45) Date of Patent: Nov. 3, 2015

(54) DENTAL WEDGE WITH TOOTH GUARD AND METHOD OF RESTORING A TOOTH USING THE SAME

(75) Inventor: Simon P. McDonald, Katikati (NZ)

(73) Assignee: DENTSPLY International Inc., York, PA (US)

( * ) Notice: Subject to any disclaimer, the term of this patent is extended or adjusted under 35 U.S.C. 154(b) by 104 days.

(21) Appl. No.: 12/977,840

(22) Filed: Dec. 23, 2010

(65) Prior Publication Data

US 2012/0164597 A1 Jun. 28, 2012

(51) Int. Cl.
*A61C 7/00* (2006.01)
*A61C 5/12* (2006.01)

(52) U.S. Cl.
CPC ...................................... *A61C 5/127* (2013.01)

(58) Field of Classification Search
CPC ................................. A61C 5/127; A61C 5/125
USPC ....................... 433/136, 148–149, 155, 39–40
See application file for complete search history.

(56) References Cited

U.S. PATENT DOCUMENTS

| | | | | |
|---|---|---|---|---|
| 1,935,481 A | * | 11/1933 | Nelson | 433/39 |
| 2,782,503 A | * | 2/1957 | Thompson | 433/39 |
| 3,795,052 A | * | 3/1974 | Mowery | 433/39 |
| 4,259,070 A | * | 3/1981 | Soelberg et al. | 433/149 |
| 4,337,041 A | * | 6/1982 | Harsany | 433/149 |
| 4,578,035 A | * | 3/1986 | Pruitt | 433/149 |
| 4,718,852 A | * | 1/1988 | Galler | 433/148 |
| 5,743,738 A | * | 4/1998 | Baffelli et al. | 433/149 |
| D597,208 S | * | 7/2009 | Ericsson et al. | D24/152 |
| 2004/0248064 A1 | * | 12/2004 | Rodriguez del Val | 433/149 |
| 2007/0087310 A1 | * | 4/2007 | Giusti | 433/155 |
| 2007/0254263 A1 | * | 11/2007 | McDonald | 433/149 |

FOREIGN PATENT DOCUMENTS

| | | | | |
|---|---|---|---|---|
| DE | 3816501 A1 | * | 11/1989 | A61C 5/04 |
| EM | 406319 | | 11/2005 | |
| EM | 805684 | | 11/2007 | |
| SE | 0900081 A1 | * | 8/2010 | A61C 5/12 |
| WO | WO 2006056989 A1 | * | 6/2006 | |
| WO | WO 2010087758 A1 | * | 8/2010 | A61C 5/12 |

OTHER PUBLICATIONS

Machine Translation of DE 3816501 A1.*
Directa AB, FenderMate Informational Materials, www.directa.com, publication date unknown.

* cited by examiner

*Primary Examiner* — Cris L Rodriguez
*Assistant Examiner* — Matthew Nelson
(74) *Attorney, Agent, or Firm* — IpHorgan Ltd.

(57) ABSTRACT

The present invention relates to dental devices utilized during the restoration of teeth and more particularly a dental wedge, for use in the inter-proximal space between adjacent teeth, the dental wedge comprising: a wedge body; and a guard releasably engaged to the wedge body, wherein the guard is transformable between a first position adjoined the wedge body and a second position disengaged from the wedge body.

24 Claims, 12 Drawing Sheets

DENTAL WEDGE WITH TOOTH GUARD AND METHOD OF RESTORING A TOOTH USING THE SAME

FIELD OF INVENTION

The present invention relates to a device for use with dental matrices in the placement of dental fillings and tooth restorations.

BACKGROUND OF INVENTION

To enable the dental professional to place composite fillings, matrices are used. A matrix is a device which wraps around the tooth and acts as a mould to contain composite resins before they are cured. Matrices are generally formed of plastic or stainless steel and are either circumferential or sectional. Sectional matrices fit only in one proximal area of the tooth while circumferential matrix bands fit around the entire circumference of the tooth. Matrices are secured in place by the use of wedges and/or clamps. The prior art wedges are generally made of wood or plastic and are placed between the matrix and an adjacent tooth. Wedges are used to hold the matrix against the tooth being filled and to temporarily separate the tooth being filled and the adjacent tooth.

Preparing for a class II filling poses a major risk of damaging the adjacent tooth. Various studies have concluded that adjacent teeth are damaged during such preparation in anywhere from 66-90% of all cases. Metal shields have been employed to provide a barrier between adjacent teeth during preparation for the filling. However, the shield on many protection devices loosens when the approximal contact point is cut away, thus increasing the risk of accidental aspiration of the shield. In addition, shields in prior art devices must be removed and discarded upon completion of the preparation phase and replaced with a traditional dental wedge during the restoration phase.

SUMMARY OF INVENTION

The present invention addresses the shortcomings exhibited in the prior art by comprising a multi-use device suitable for use during the filling preparation phase and restoration phase. The present invention comprises a dental wedge, for use in the inter-proximal space between adjacent teeth, the dental wedge comprising: a wedge body; and a guard releasably engaged to the wedge body, wherein the guard is transformable between a first position adjoined the wedge body and a second position disengaged from the wedge body. The guard further comprises a plurality of extensions on the bottom edge of the guard that engage a spine of the wedge body having a thickness sufficient to securely receive the extensions of the guard and retain the guard in position.

The present invention further relates to a method of restoring a tooth comprising: (a) an insertion step wherein a dental wedge consisting of the wedge body and a tooth guard is inserted into a restoration area with the wedge body advancing into the inter-proximal space between a first and a second adjacent tooth and guard advancing in between the first and second adjacent tooth; (b) a preparation step wherein the first tooth is prepared for the restoration and the second tooth is partitioned from the first tooth by the tooth guard; and (c) a removal step wherein the guard is disengaged from the wedge body and removed from the restoration area and wedge body remains in the inter-proximal space between the first and second adjacent tooth. The method further consists of a matrix placement step wherein a dental matrix is inserted between the first and second adjacent tooth and wedge body secures the dental matrix in place.

DETAILED DESCRIPTION OF DRAWINGS

FIGS. 1-11 show the dental wedge 10 of the present invention. The inventive dental wedge 10 prevents a bur from nicking the adjacent tooth by incorporating a guard 12 utilized during tooth preparation that forms a partition between a first and second adjacent tooth that is detached from a wedge body 14 during the restoration of the damaged tooth. The detachable guard 12 results in the wedge body 14 staying in place in the inter-proximal space between the first and second adjacent tooth during the preparation and restoration phases. This, in turn, reduces bleeding of the papilla as disruption of the tissue from insertion of multiple devices specific to each step of the restoration process is avoided. Because the risks of nicking adjacent teeth during the preparation phase are reduced or eliminated through use of the present invention, the time of the preparation phase and precision required by the dental professional is also reduced.

Figure 1:
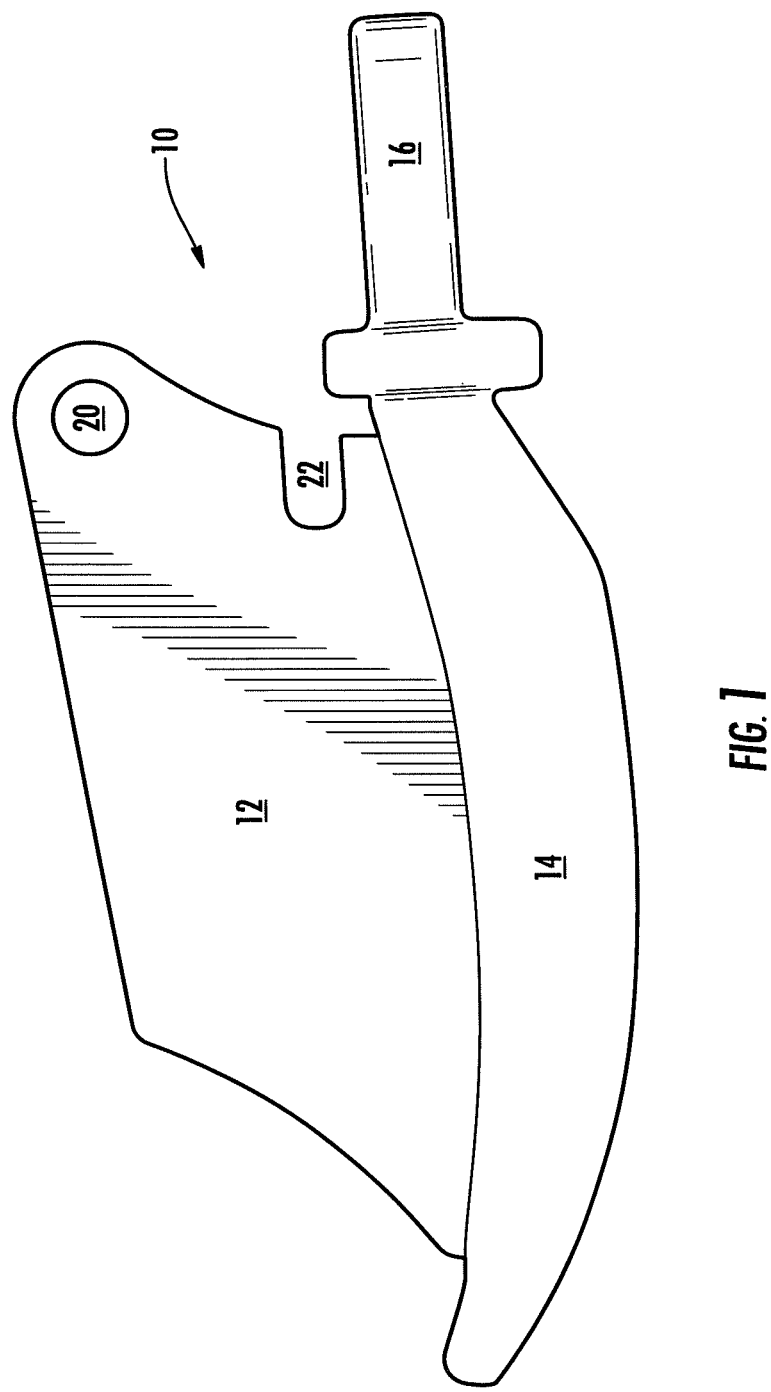
FIG. 1 is a side elevation view of a dental wedge with a tooth guard according to the present invention.
Figure 2:
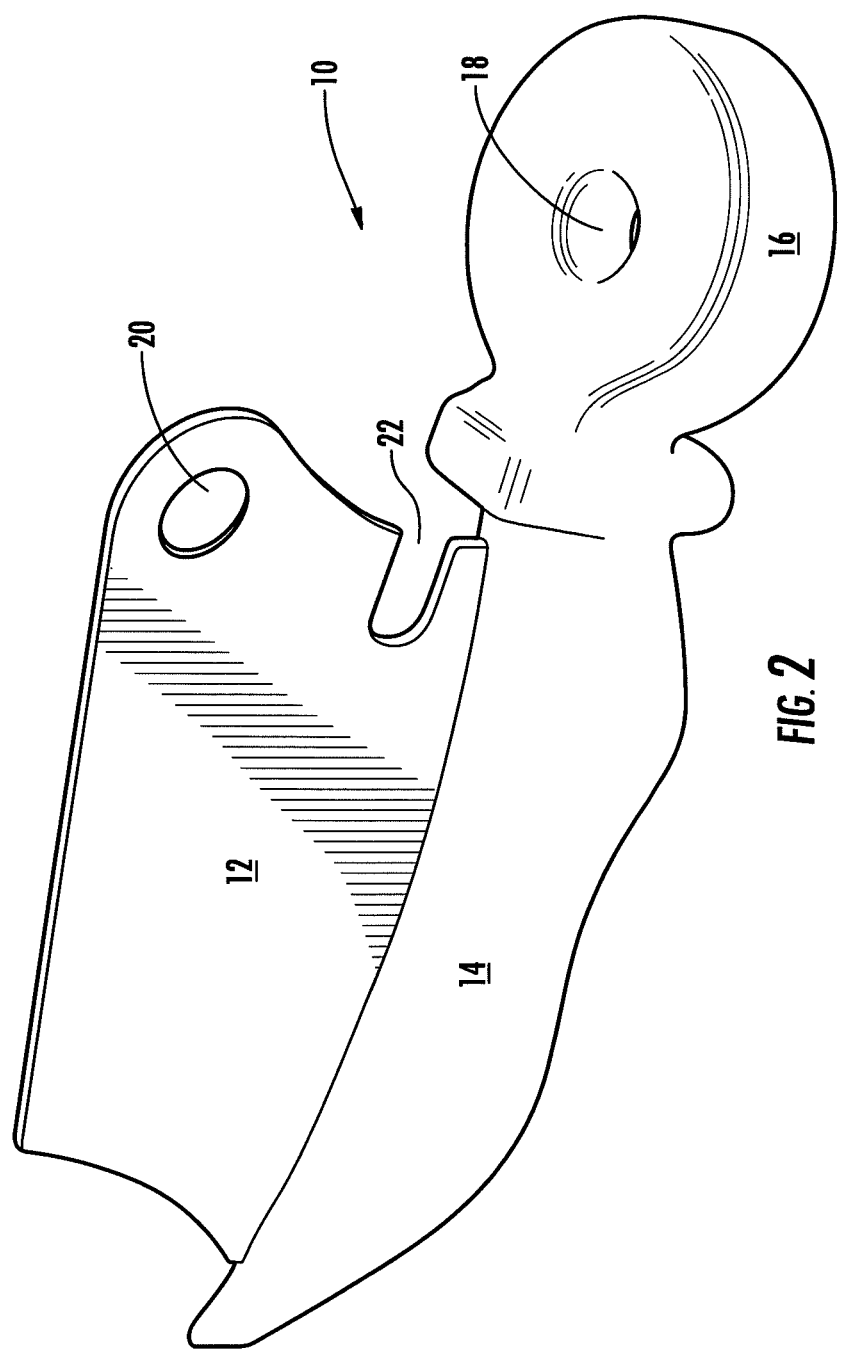
FIG. 2 is a perspective view of a dental wedge with a tooth guard according to the present invention.
Figure 3:
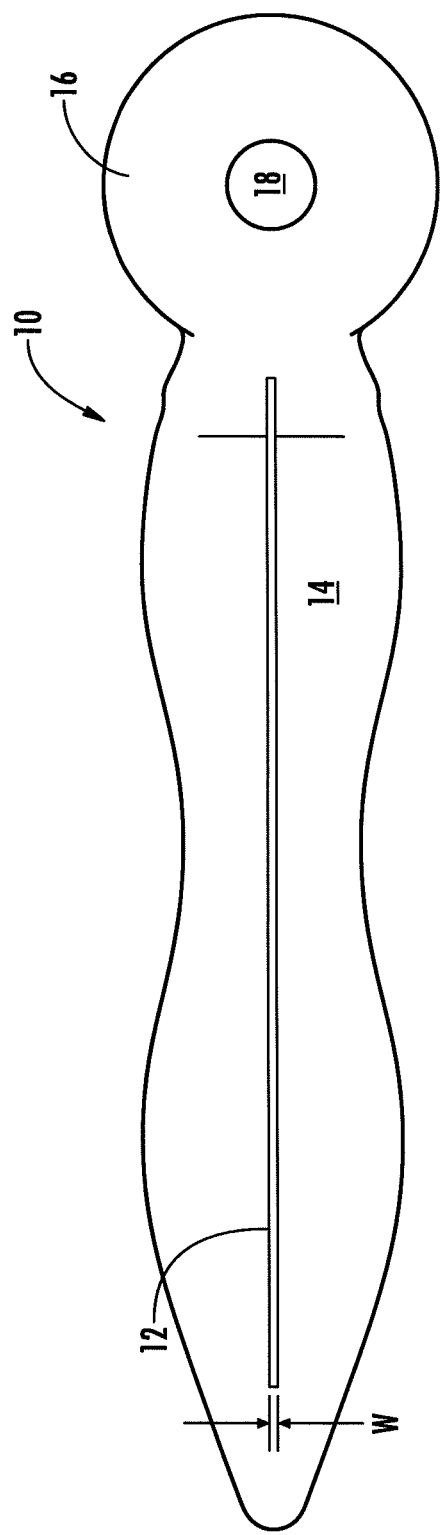
FIG. 3 is a top plan view of a dental wedge with a tooth guard according to the present invention.
Figure 4:
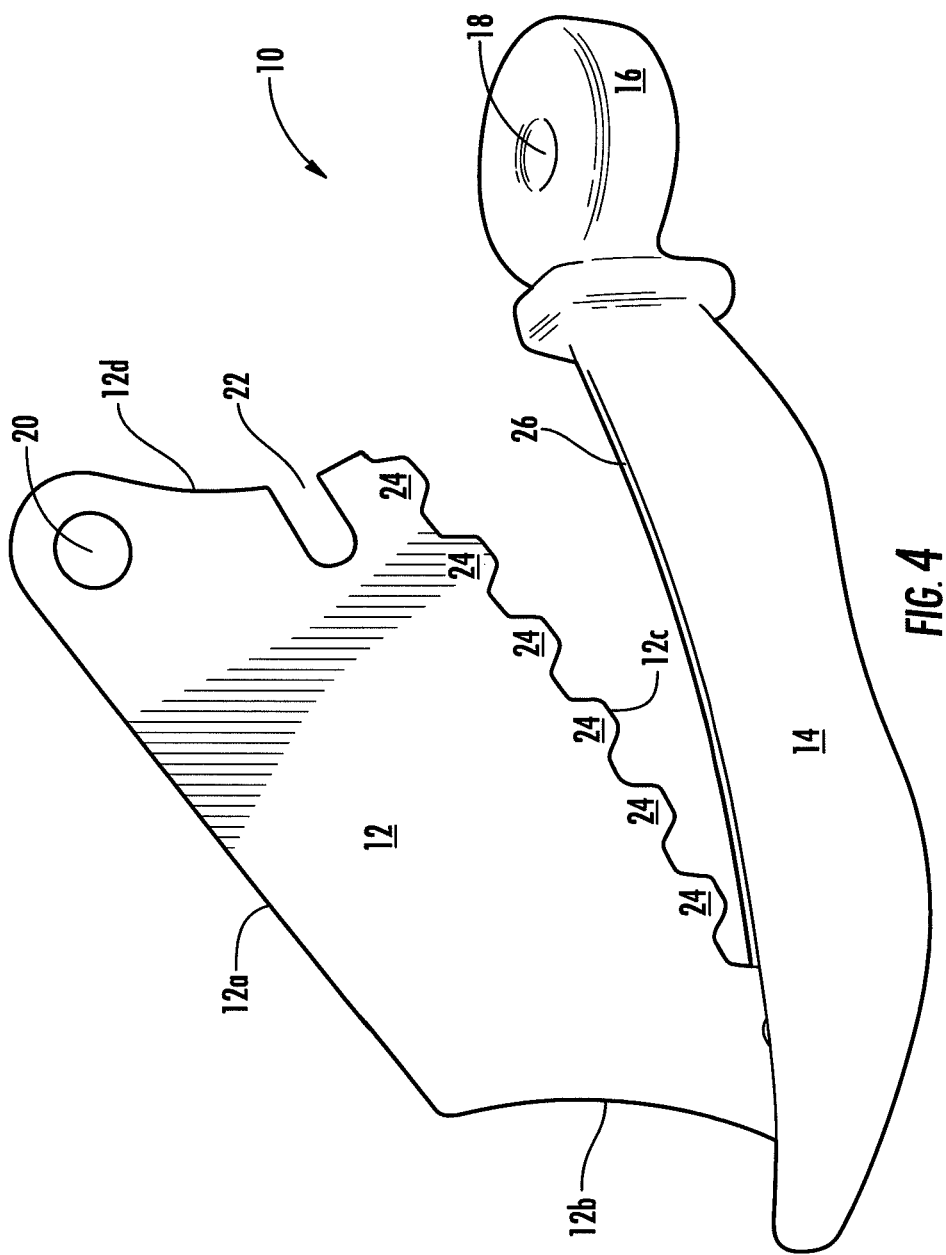
FIG. 4 is another perspective view of a dental wedge with a tooth guard according to the present invention.

Turning to FIGS. 1-4, the basic elements and structure of the inventive dental wedge 10 are shown. The dental wedge 10 comprises a detachable guard 12 releasably adjoined to a wedge body 14. A handle 16 adjacent the wedge body 14 may be integrally formed, molded, or cast with the wedge body 14 or may be formed, molded, or cast separately from the wedge body 14 and affixed thereto in a separate process. The handle 16 may be gripped directly by a dental instrument and also includes a bore 18 configured for gripping the dental wedge 10 with a dental instrument having a pinned gripping portion. The guard 12 may also include a bore 20 or notch 22 configured for gripping of the guard with a dental instrument having a pinned gripping portion. The notch 22 may also receive a bladed dental instrument. As shown in FIG. 3, the guard 12 extends along the length of the wedge body 14 and, in this embodiment, the guard 12 is aligned along the midline of the wedge body 14.

Figure 5:
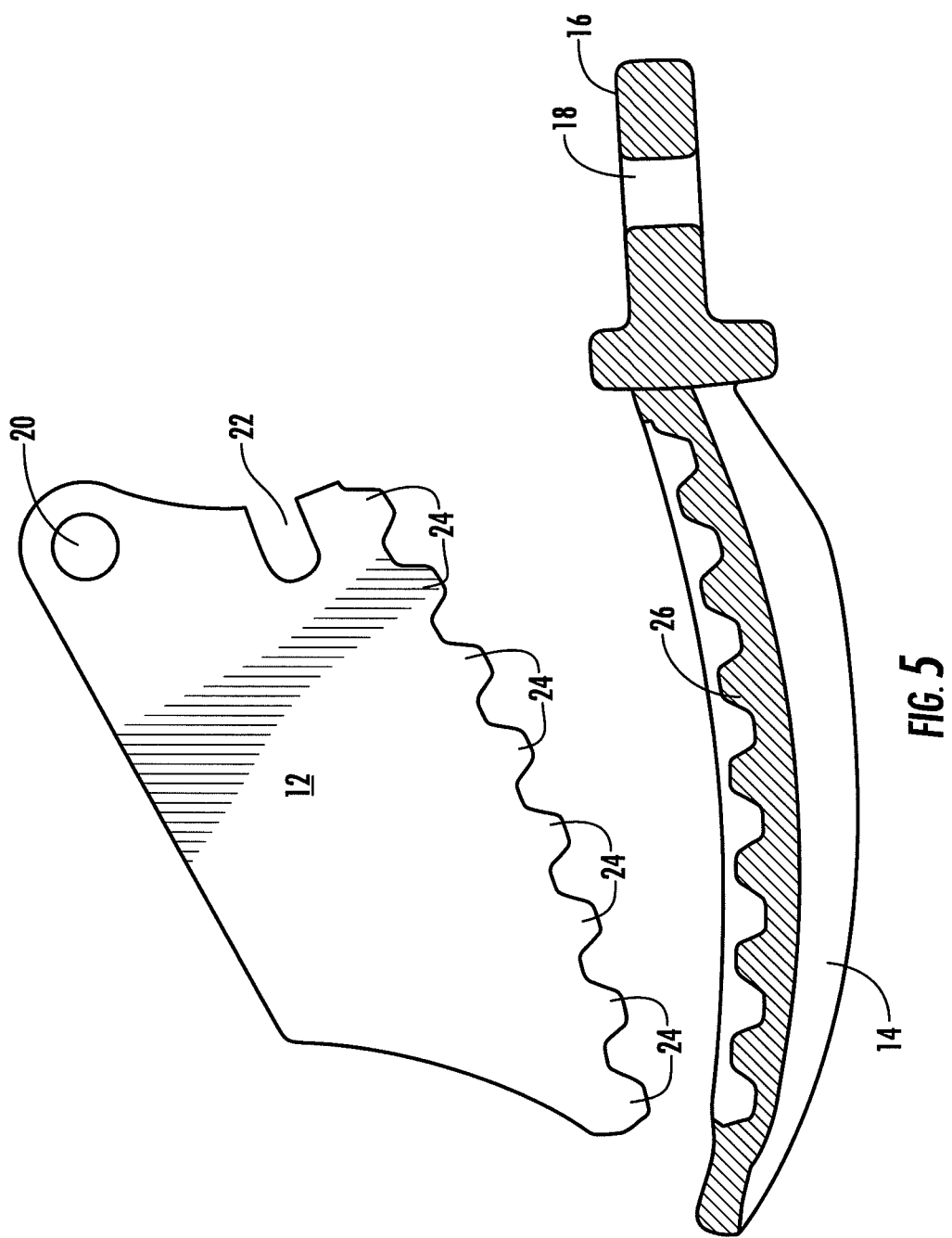
FIGS. 5-7 is a partial cutaway side elevation view of a dental wedge with a tooth guard according to the present invention.
Figure 6:
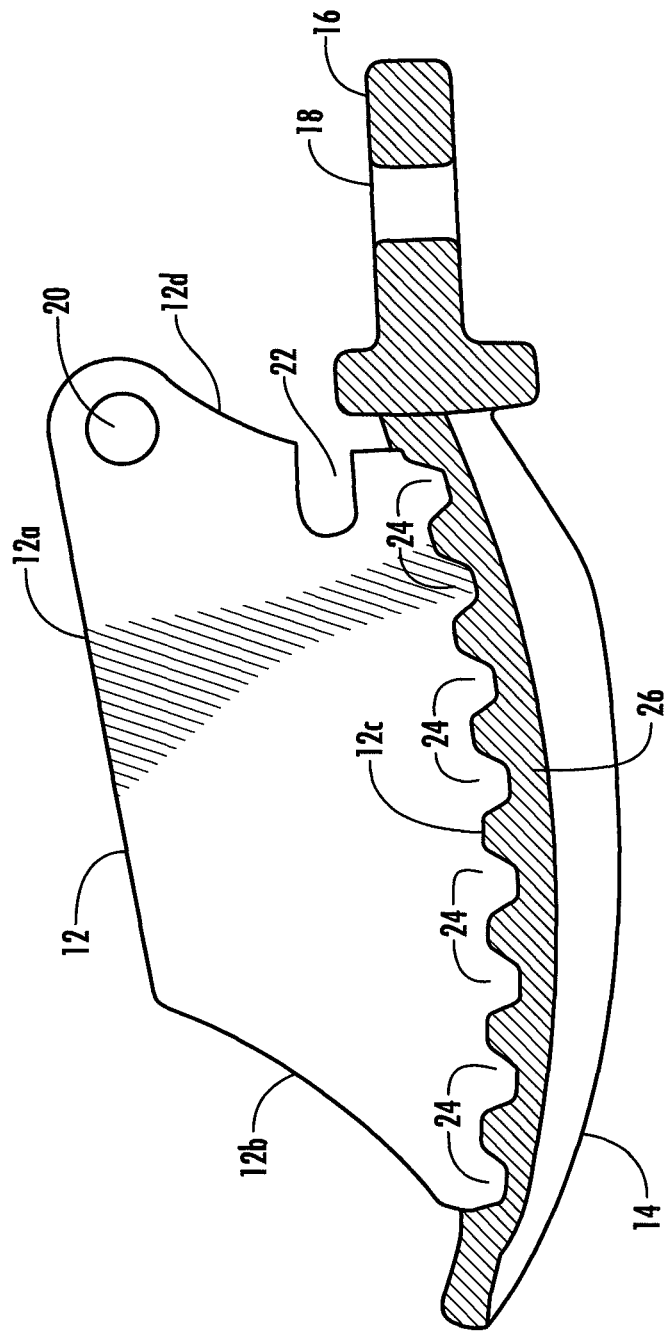
Figure 7:
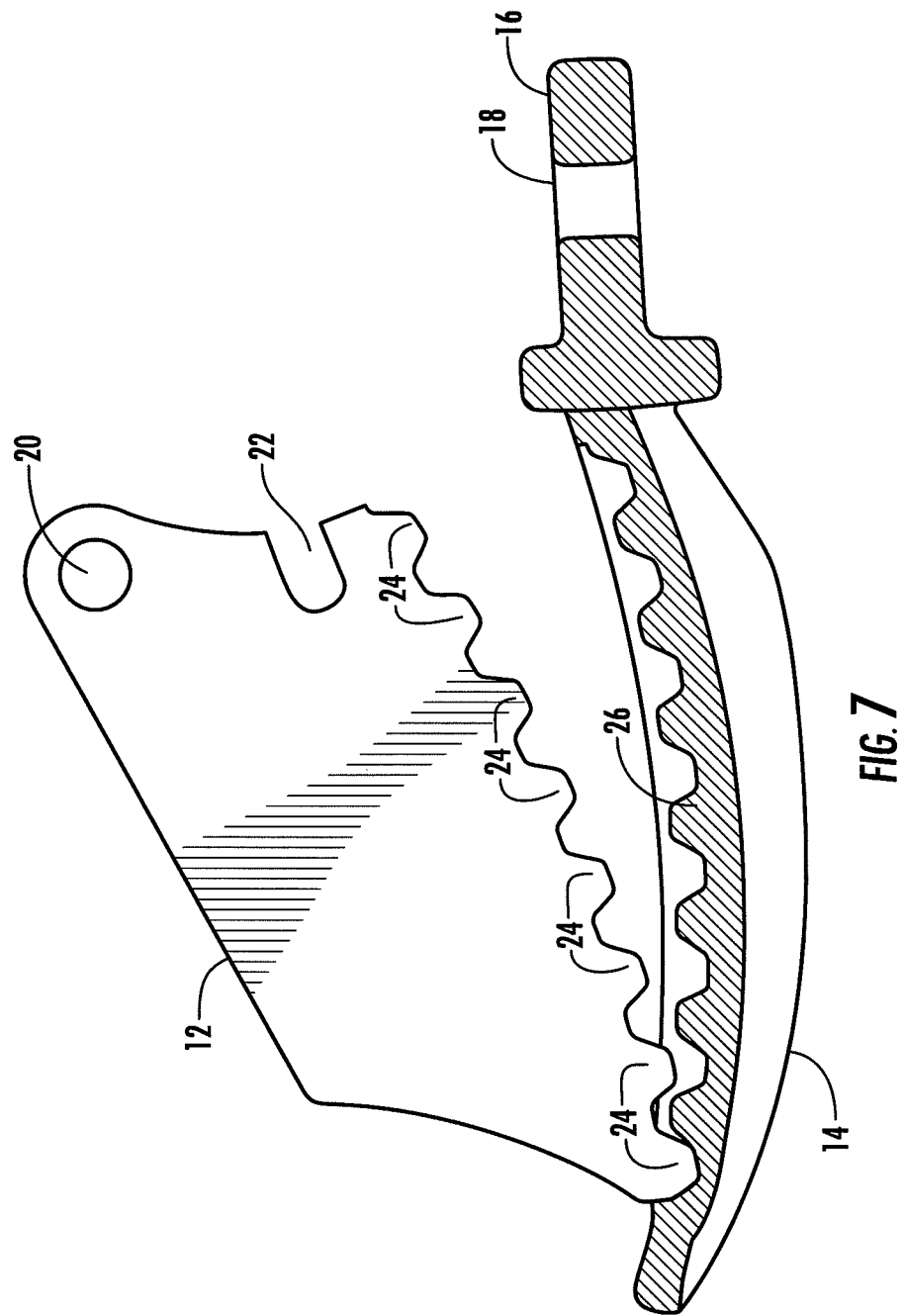

FIGS. 5-7 show the interface between the guard 12 and wedge body 14 in greater detail. The bottom edge of the guard 12 consists of a plurality of extensions 24 that anchor the guard 12 to the wedge body 14. As shown in these figures, the extensions 24 comprise a plurality of tabs. In one embodiment of the present invention, the wedge body 14 is formed, molded or cast around the extensions 24 of the guard 12 to provide an interference engagement between the guard 12 and wedge body 14. To accommodate the extensions 24, the wedge body 14 includes a spine 26 of sufficient depth to enable the guard 12 to be securely adjoined with the wedge body 14 and to provide structural integrity to the dental wedge 10 once the guard 12 is disengaged from the wedge body 14. To accomplish this, the depth of the spine 26 is at least as great as the length of the extensions 24. The wedge body 14 is formed from a material sufficient to perform these multiple functions. Such materials may include SANTOPRENE™ thermoplastic vulcanates from Advanced Elastomer Systems, polypropylene or polyethylene. Materials are selected based on the desired application of the dental wedge and required hardness of the material.

In the embodiment shown in FIG. 6, the guard 12 is substantially quadrilateral in configuration having a top edge 12a, front edge 12b, bottom edge 12c, and rear edge 12d. The overall size and configuration of the guard 12 is selected to achieve the desired function of protecting the adjacent tooth from damage during preparation of the restored tooth while causing minimal obstruction to the dentist's access to the restoration area and being minimally invasive to the patient. The top edge 12a is substantially flat to avoid jagged edges or points where dental instruments or dressing could become caught, snagged or torn during the restoration. The bottom edge 12c is generally comprised of the plurality of extensions 24 and may exhibit a generally curved configuration to mirror any curvature present in the wedge body 14. The length of the bottom edge 12c of the guard 12 is less than the length of the spine 26 of the wedge body 14. This enables the dental wedge 10 to require initial alignment of only the wedge body 14 during insertion into the inter-proximal space between adjacent teeth. Once the wedge body 14 is properly aligned with the inter-proximal space, the guard 12 is self-aligning with the space between the adjacent teeth and will insert there between as the wedge body 14 advances through the inter-proximal space.

The front edge 12b or leading edge is configured to enable gradual introduction of the guard 12 into the inter-proximal space and between adjacent teeth. Preferably this is accomplished by configuring the front edge 12b with a curved profile. The curved front edge 12b also enables ease of advancement of the dental wedge 10 between adjacent teeth. The offsetting of the shield 12 from the front of the wedge body 14 and the curved profile of the front edge 12b enables the wedge body 14 to extend further through the inter-proximal space without concern that the guard 12 will come into contact with the patient's tongue. An increase in contact area between the guard 12 and wedge body 14 further stabilizes the guard without causing undue irritation or nuisance to the patient is also a result of the curved front edge 12b that will minimize interaction between the patient's tongue and the guard 12. As shown in FIG. 3, the width W of the guard 12 is substantially less than the width of the wedge body 14. The rear edge 12d or trailing edge of the guard 12 may also have a curved profile.

Figure 8:
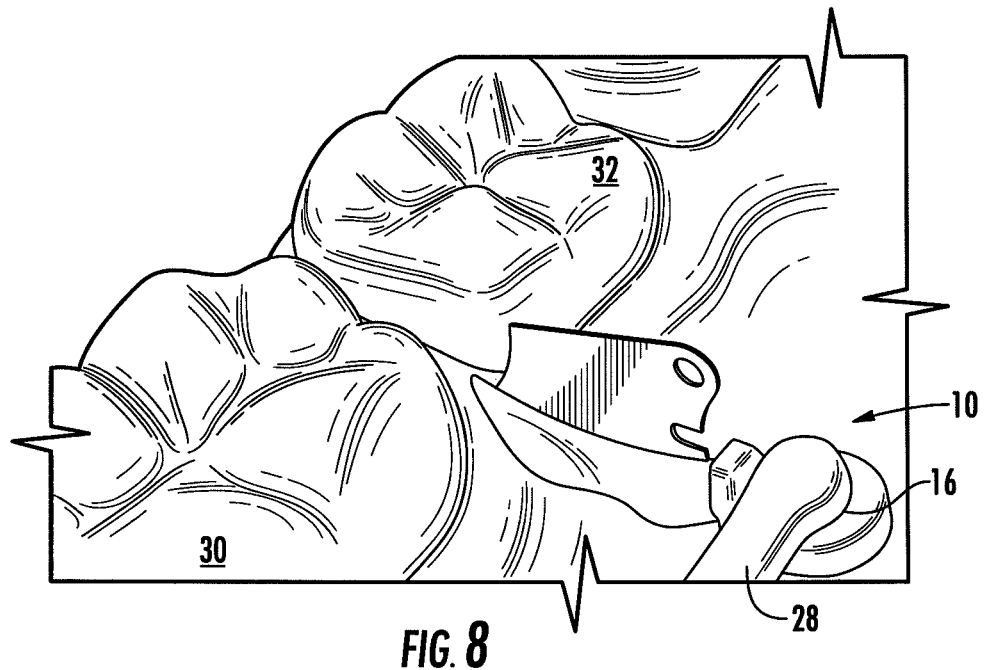
FIGS. 8-11 are perspective views of a dental wedge with a tooth guard in operation.

FIGS. 8-11 show the inventive dental wedge 10 in operation. First, in the "Insertion" phase, the dental wedge 10 is inserted between adjacent teeth 30, 32. As shown in FIG. 8, the dental wedge 10 is gripped at the handle 16 by a dental instrument 28. The guard 12 is in a first position adjoined to the wedge body 14 and forms a partition or protective barrier between the first and second adjacent teeth 30, 32 and the wedge body 14 advances into the inter-proximal space between the first and second teeth 30, 32. In FIG. 8, the dental instrument 28 includes a pin portion that grips the handle 16 at the bore (not seen) to assist in maneuvering and positioning of the dental wedge 10 within the restoration area.

Figure 9:
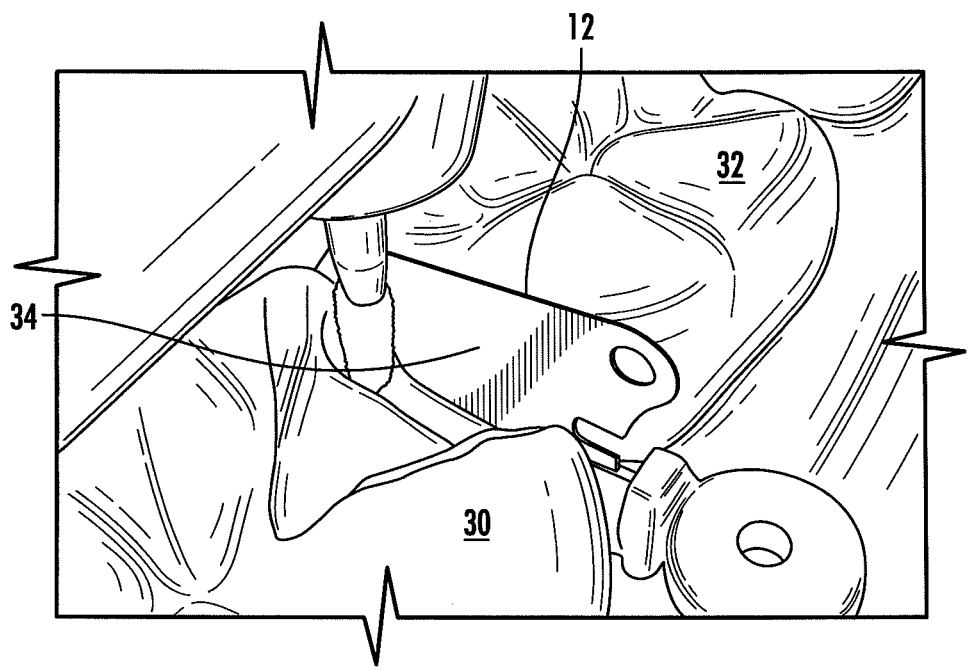
Figure 10:
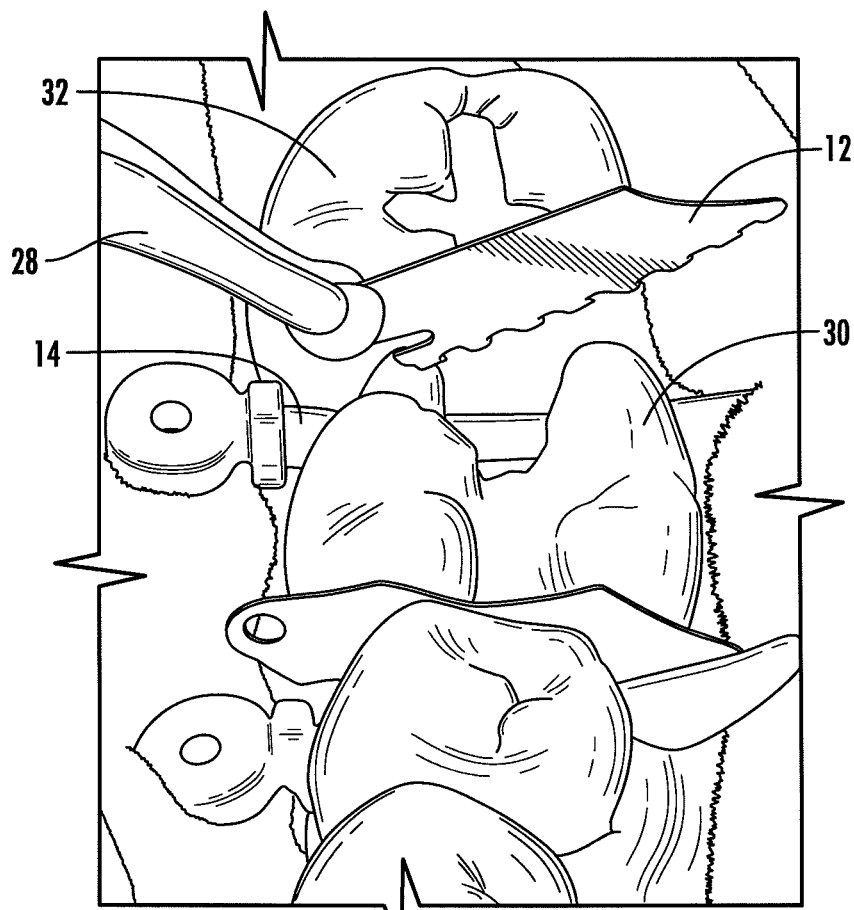
Figure 11:
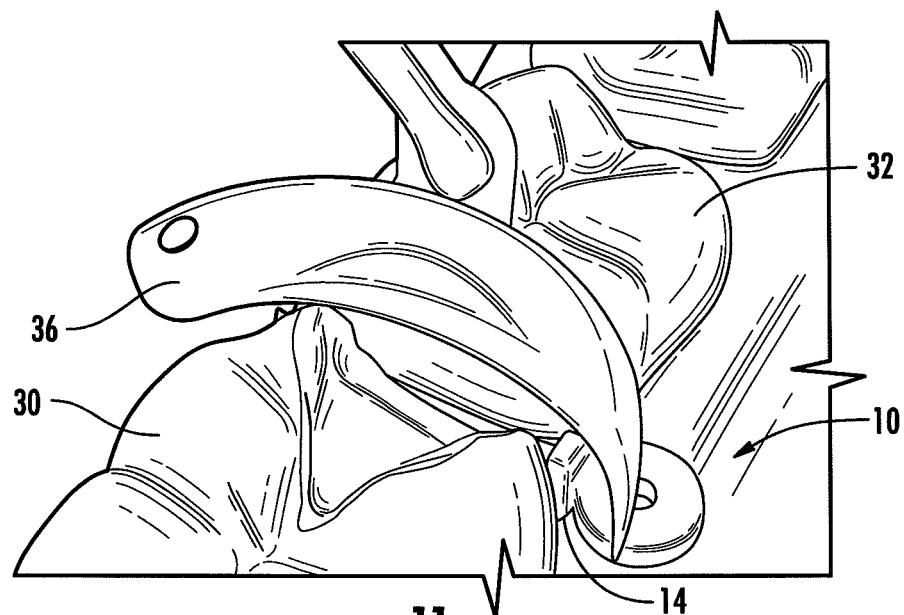

The "Restoration" phase is shown in FIG. 9. The guard 12 separates the tooth being restored 30 from the adjacent tooth 32. The dental professional uses a bur 34 to prepare the tooth to be restored 30 with reduced concerns of inadvertently nicking the adjacent tooth 32 with the bur 34. In the "Removal" phase, shown in FIG. 10, the guard 12 is disengaged from the wedge body 14 and removed from the restoration area. As seen in this figure, a dental instrument 28 is used to grab the guard 12 at the bore (not seen). As the guard 12 is lifted away from the wedge body 14, the bond between guard 12 and the wedge body 14 is broken and the guard 12 is removed from the restoration area. Alternatively, the tip of a flat-bladed dental instrument is inserted into the notch in the guard and is used to lever the guard 12 away from the wedge body 14, using the front end of the wedge body 14 as a pivot point. The guard 12 disengages from the wedge body 14 and is then grabbed with a dental instrument at the bore and removed from the restoration area. In this manner, the guard 12 is transformable between the first position adjoined the wedge body 14 and a second position disengaged from the wedge body 14. FIG. 11 shows the "Matrix Placement" phase during which a matrix band 36 is placed between the adjacent teeth 30, 32. The wedge body 14 remains in place in the inter-proximal space between the first and second teeth 30, 32 and secures the matrix 36 in place forming at tight margin between the matrix 36 and tooth to be restored 30.

The concepts of the inventive dental wedge described herein may be embodied in dental wedges having wedge bodies exhibiting a number of cross-sectional shapes or configurations, provided that there is a spine or landing area sufficient to receive and releasably engage the guard. FIGS. 1-11 demonstrate a wedge body 14 having a spine and a first and second side each side converging towards the spine, as shown in greater detail in FIGS. 12-17. Further details of the wedge body 14 are also disclosed in U.S. application Ser. No. 11/703,189 to the same inventor, the contents of which are incorporated herein by reference.

Figure 12:
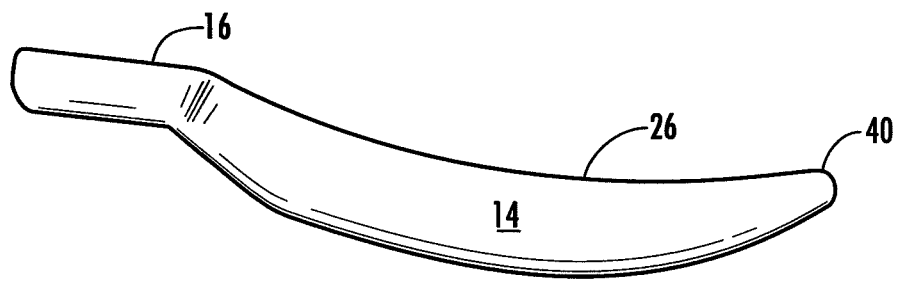
FIG. 12 is a side elevation view of a component of an embodiment of the present inventive dental wedge.
Figure 13:
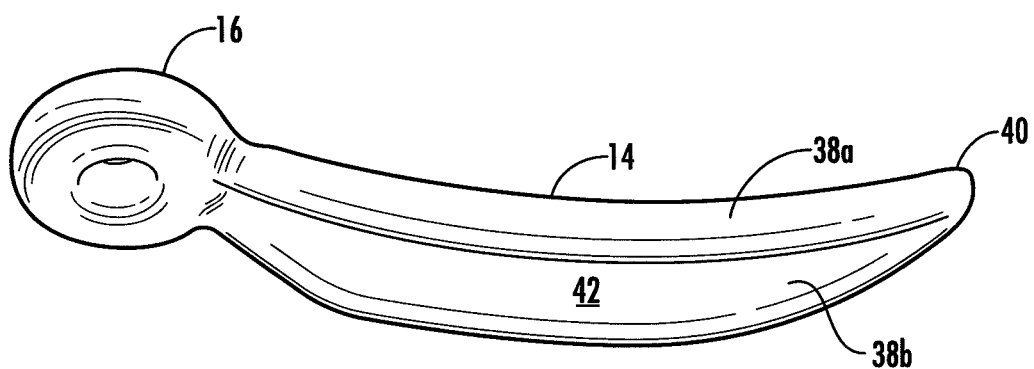
FIG. 13 is a perspective view of a component of an embodiment of the present inventive dental wedge.
Figure 14:
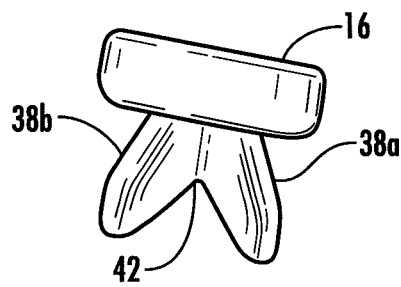
FIG. 14 is a rear elevation view of a component of an embodiment of the present inventive dental wedge.

FIGS. 12-18 show a wedge body 14 with a spine 26 extending along the top of the wedge body 14 from the handle 16 to a tapered tip 40 and provides the area for adjoining the guard to the wedge body 14. As seen in FIG. 12, the wedge body 14 when viewed from the side has a curved profile. The tapered tip 40 is blunt to help prevent damage when the dental wedge 10 is inserted between adjacent teeth. When viewed from the underside, as seen in FIGS. 13 and 14, the wedge body 14 includes a hollow or open-sided void 42 enabling the sidewalls 38a, 38b to flex towards each other within the open-sided void 42 as the dental wedge 10 advances into the space between adjacent teeth. FIG. 14 demonstrates the substantially inverted V-shape of the cross section of the wedge body 14. The sides 38a, 38b extend to the spine 26 forming an angle preferably between 25° and 50° at the most open cross section. The sidewalls 38a, 38b are sufficiently flexible to flex together as the wedge is inserted into the inter-proximal space. The side faces of the sidewalls 38a, 38b are optional concave.

Figure 15:
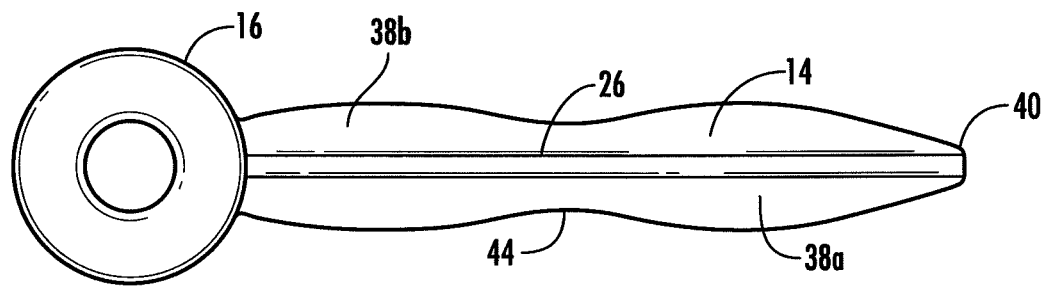
FIG. 15 is top plan view of a component of an embodiment of the present inventive dental wedge.
Figure 16:
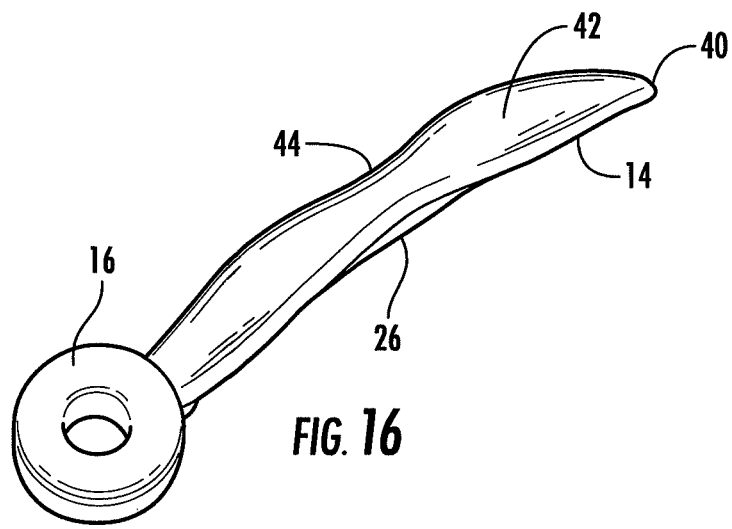
FIG. 16 is a bottom perspective view of a component of an embodiment of the present inventive dental wedge.
Figure 17:
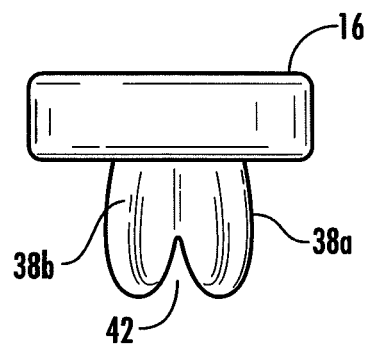
FIG. 17 is rear elevation view of a component of an embodiment of the present inventive dental wedge.
Figure 18:
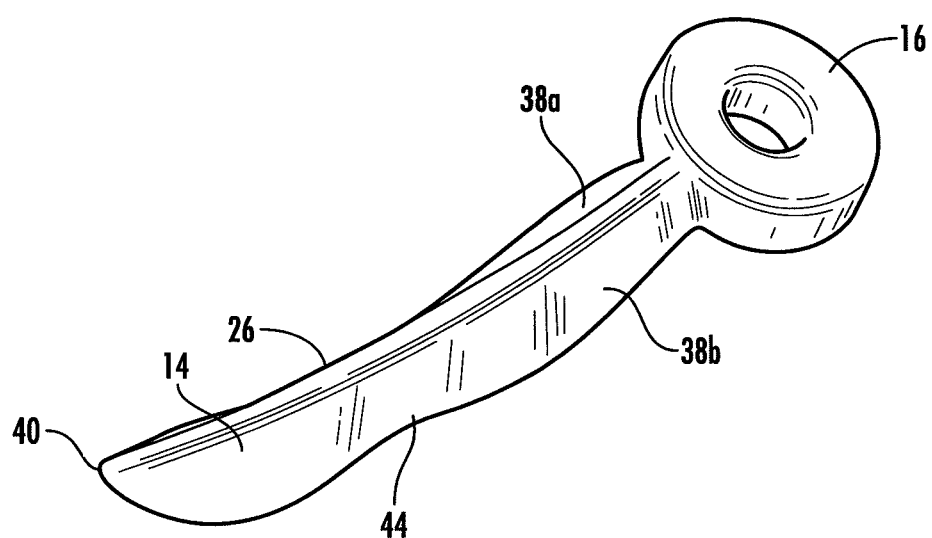
FIG. 18 is a top perspective view of a component of an embodiment of the present inventive dental wedge.

In another embodiment, shown in FIGS. 15-18, the wedge body 14 has a narrow mid section/portion 44. The narrow mid-portion/mid-section 44 is designed to replicate the inter-proximal space between adjacent teeth more accurately. A wedge body 14 with a narrow mid section/portion 44 when viewed in a plan view, as seen in FIGS. 15 and 18, looks like a wave. The contour of the wedge transitions smoothly between the different width sections.

A dental wedge 10 incorporating a wedge body 14 in the configurations shown in FIGS. 12-18 is advantageous over the prior art in that the mid-section of the wedge body 14 is flexible, allowing the dental wedge 10 to seal the gingival margin of the matrix band at both the buccal and lingual side. The curvature of the sidewalls 38a, 38b of the wedge body 14 enables the dentist to insert the dental wedge 10 into the inter-proximal space between adjacent teeth without it piercing the gingival papilla on the other side. The use of a V-shaped cross-section increases the wedge flexibility and provides a space for the gingival tissues.

While the present invention has been described in connection with a specific application, this application is exemplary in nature and is not intended to be limiting on the possible applications of this invention. It will be understood that modifications and variations may be effected without departing from the spirit and scope of the present invention. It will be appreciated that the present disclosure is intended as an exemplification of the invention and is not intended to limit the invention to the specific embodiments illustrated and described. The disclosure is intended to cover, by the appended claims, all such modifications as fall within the scope of the claims.

I claim:

1. A dental wedge, for use in the inter-proximal space between adjacent teeth, each of the adjacent teeth having a gingival margin and an occlusal surface, the dental wedge comprising:
   a wedge body;
   a planar dental bur guard releasably engaged to the wedge body, the dental bur guard including a bottom boundary, a top edge opposite the bottom boundary, and a front edge and back edge extending between the top edge and bottom boundary and extending away from the wedge body towards the occlusal surfaces of the adjacent teeth and away from the gingival margins of the adjacent teeth;
   a plurality of extensions disposed along the bottom boundary of the dental bur guard, the plurality of extensions in mating engagement with a spine of the wedge body and adapted to releasably anchor the dental bur guard to the wedge body,
   wherein the dental bur guard is transformable between a first position adjoined to the wedge body and inserted in the inter-proximal space between the adjacent teeth and a second position disengaged from the wedge body and removed from the inter-proximal space between the adjacent teeth.

2. The dental wedge of claim 1 further including a handle.

3. The dental wedge of claim 2 wherein the handle includes a dental instrument receiving bore.

4. The dental wedge of claim 1 wherein the spine is of a thickness sufficient to securely receive the plurality of extensions of the dental bur guard.

5. The dental wedge of claim 1 wherein the wedge body further includes a tip and the front edge of the dental bur guard is set back from the tip.

6. The dental wedge of claim 1 wherein the dental bur guard further includes a curved front edge.

7. The dental wedge of claim 6 wherein the wedge body further includes a tip and a front edge of the dental bur guard curves away from the tip.

8. The dental wedge of claim 1 wherein the dental bur guard and wedge body each have a first length and the first length of the dental bur guard is less than the length of the wedge body.

9. The dental wedge of claim 1 wherein the dental bur guard includes a dental instrument receiving bore.

10. The dental wedge of claim 1 wherein the dental bur guard includes a dental instrument receiving notch.

11. The dental wedge of claim 1 wherein the wedge body comprises flexibly spaced sidewalls extending from spine where the dental bur guard is adjoined to the wedge body and wherein the flexibly spaced sidewalls define an open-ended hollow space in the interior of the wedge body.

12. The dental wedge of claim 1 wherein the dental bur guard extends upwards from the wedge body and above the occlusal surfaces of the adjacent teeth.

13. The dental wedge of claim 1 wherein the dental bur guard is transformable between a first position adjoined to the wedge body and the dental bur guard and wedge body combination is inserted in the inter-proximal space between the adjacent teeth and a second position disengaged from the wedge body wherein the wedge body remains in the inter-proximal space and the dental bur guard is removed from the inter-proximal space between the adjacent teeth.

14. The dental wedge of claim 1 wherein the dental bur guard forms a continuous boundary between adjacent teeth from the front edge and to the back edge of the dental bur guard as the dental bur guard extends from a first end of the wedge body towards a second end of the wedge body.

15. A method of restoring a tooth comprising:
   a. an insertion step wherein a dental wedge consisting of the wedge body and a planar dental bur guard removably attached to the wedge body is inserted into a restoration area with the wedge body advancing between a first and a second adjacent tooth at the gingival margin of the teeth and the dental bur guard advancing between the first and second adjacent tooth in the inter-proximal space;
   b. a preparation step wherein the first tooth is prepared for restoration by removing a first section of the first tooth and the second tooth is partitioned from the first tooth by the tooth dental bur guard; and
   c. a removal step wherein the dental bur guard is disengaged from the wedge body and removed from the restoration area and the wedge body remains between the first and second adjacent tooth at the gingival margin of the teeth.

16. The method of restoring a tooth of claim 15 further consisting of a matrix placement step wherein a dental matrix is inserted between the first and second adjacent tooth and wedge body secures the dental matrix in place.

17. The method of claim 15 wherein the removal step consists of engaging a bore in the dental bur guard with a dental instrument and disengaging the dental bur guard from the wedge body and removing it from the restoration area with the dental instrument.

18. The method of claim 15 wherein the removal step consists of engaging a notch in the dental bur guard with a dental instrument and disengaging the dental bur guard from the wedge body.

19. The method of claim 15 further comprising removing the wedge body from the inter-proximal space and restoration area.

20. A dental wedge, for use in the inter-proximal space between adjacent teeth, each of the adjacent teeth having a gingival margin and an occlusal surface, the dental wedge comprising:
 a wedge body;
 a planar dental bur guard releasably engaged to the wedge body, the dental bur guard including a bottom boundary, a top edge opposite the bottom boundary, and a front edge and back edge extending between the top edge and bottom boundary and extending away from the wedge body towards the occlusal surfaces of the adjacent teeth and away from the gingival margins of the adjacent teeth;
 a first extension disposed along the bottom boundary of the dental bur guard, the first extension in mating engagement with a spine of the wedge body and adapted to releasably anchor the dental bur guard to the wedge body, wherein the dental bur guard is transformable between a first position adjoined to the wedge body and inserted in the inter-proximal space between the adjacent teeth and a second position disengaged from the wedge body and removed from the inter-proximal space between the adjacent teeth.

21. The dental wedge of claim 20 further including a handle having a dental instrument receiving bore.

22. The dental wedge of claim 20 wherein the wedge body further including a tip and the front edge of the dental bur guard is set back from the tip and curves away from the tip.

23. The dental wedge of claim 20 wherein the wedge body comprises flexibly spaced sidewalls extending from spine where the dental bur guard is adjoined to the wedge body and wherein the flexibly spaced sidewalls define an open-ended hollow space in the interior of the wedge body.

24. The dental wedge of claim 20 wherein the dental bur guard forms a continuous boundary between adjacent teeth from the front edge and to the back edge of the dental bur guard as the dental bur guard extends from a first end of the wedge body towards a second end of the wedge body.

* * * * *